United States Patent [19]

Hunziker et al.

[11] 4,406,900
[45] Sep. 27, 1983

[54] NEUROLEPTIC USE OF MORPHANTHRIDINES

[75] Inventors: Fritz Hunziker, Berne; Rudolf Fischer, Kehrsatz, both of Switzerland

[73] Assignee: Sandoz Ltd., Basel, Switzerland

[21] Appl. No.: 304,357

[22] Filed: Sep. 22, 1981

Related U.S. Application Data

[60] Division of Ser. No. 111,459, Jan. 11, 1980, Pat. No. 4,308,207, which is a continuation-in-part of Ser. No. 912,496, Jun. 5, 1978, abandoned, which is a continuation of Ser. No. 848,498, Nov. 4, 1977, abandoned.

[51] Int. Cl.³ .......................................... A61K 31/38
[52] U.S. Cl. ................................................. 424/250
[58] Field of Search ..................... 260/243, 3; 424/250

*Primary Examiner*—Donald G. Daus
*Assistant Examiner*—D. B. Springer

*Attorney, Agent, or Firm*—Gerald D. Sharkin; Robert S. Honor; Joseph J. Borovian

[57] ABSTRACT

Compounds of formula I,

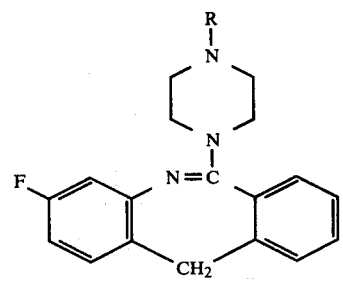

wherein R is hydrogen, alkyl ($C_{1-4}$) or hydroxyalkyl ($C_{2-3}$), are useful as neuroleptics, sleep promoters, myotonolytics, and anti-depressants.

3 Claims, No Drawings

NEUROLEPTIC USE OF MORPHANTHRIDINES

This is a division of application Ser. No. 111,459 filed Jan. 11, 1980, now issued as U.S. Pat. No. 4,308,207, which in turn is a continuation-in-part of Ser. No. 912,496, filed June 5, 1978, now abandoned, which in turn is a continuation of Ser. No. 848,498, filed Nov. 4, 1977, now abandoned.

The invention relates to morphanthridine derivatives.

The present invention provides compounds of formula I,

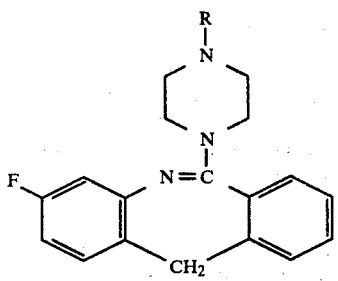

wherein R is hydrogen, alkyl ($C_{1-4}$) or hydroxyalkyl ($C_{2-3}$).

R is preferably alkyl which preferably has 1 or 2 carbon atoms. The hydroxyl of the hydroxyalkyl group is preferably in the terminal position. The hydroxyalkyl group is preferably hydroxyethyl.

The present invention provides a process for the production of a compound of formula I which comprises reacting a compound of formula II,

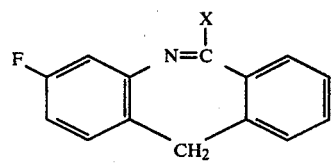

wherein X is a leaving group,
with a compound of formula III,

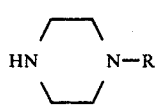

wherein R is as defined above.

The reaction may be effected in conventional manner for the production of similar compounds. X is preferably chlorine.

The process may be conveniently effected at a temperature of from 50° to 170° C. in an inert organic solvent such as xylene or dioxane.

A compound of formula II may be produced in known manner from 3-fluoro-5,6-dihydromorphanthridin-6-one and may be reacted further without purification.

Free base forms of the compounds of formula I may be converted into acid addition salt forms in conventional manner and vice versa. Suitable acids for salt formation include hydrochloric acid or fumaric acid.

In the following Examples all temperatures are in degrees Centigrade and are uncorrected.

EXAMPLE 1:
3-fluoro-6-(4-methyl-1-piperazinyl)morphanthridine 5 g 3-fluoro-5,6-dihydromorphanthridin-6-one, 80 ml phosphorus oxychloride and 2 ml N,N-dimethylaniline are boiled for 4 hours. The excess phosphorus oxychloride is distilled off in a vacuum and the residue is partitioned between ice-water and xylene. The xylene phase is washed with dilute hydrochloric acid and water. The xylene phase is dried over sodium sulphate. The resultant solution containing the imidochloride of the above lactam is concentrated to 50 ml and boiled with 6 ml N-methylpiperazine for 4 hours.

The cooled reaction mixture is treated with water, made alkaline with concentrated sodium hydroxide solution and extracted with ether. The ether phase is washed with water and extracted with dilute hydrochloric acid. The acid phase is made alkaline and shaken with ether. The ether phase is dried over sodium sulphate, and concentrated, and petroleum ether is added when only a little volume remains whereupon the title compound in free base form of M.Pt. 118°–119° crystallizes out.

EXAMPLE 2

In analogous manner to that described in Example 1 the following compounds of formula I may be produced wherein:

| Example | R | M.Pt. |
|---------|---|-------|
| (a) | H | 118°–120° |
| (b) | CH₂CH₂OH | 160°–161° |

The compounds of formula I are useful because they exhibit pharmacological activity in animals.

The compounds are useful as neuroleptic agents, e.g. for the treatment of psychoses and neuroses as indicated in standard tests. For example, the compounds on administration of from 0.01 to 10 mg/kg i.p. to mice inhibit the hypermotility induced by 4,α-dimethyl-m-tyramine (H 77/77) in the test carried out according to the principles of J. B. Lassen, Psychopharmacologia 37, 331–340 (1974). In this test, the Example 1 and 2b compounds exhibit an $ID_{50}$ of less than 1 mg/kg i.p.

Furthermore, on administration of 2–20 mg/kg p.o. of the compounds to rats in the sleep/wake cycle carried out in accordance with the principles of H. Kleinlogel et al, European J. Pharmacol. 33, 159–163 (1975) an increase in the sleep phase II is observed and a decrease in paradoxical sleep.

Additionally, an inhibition of spontaneous motility is observed in mice on p.o. administration of from 0.1 to 100 mg/kg to the compounds in accordance with the principles of Caviezel and Baillod, Pharm. Acta Helv. 33, 465–484 (1958). In this test, the Example 1 and 2b compounds exhibit an $ED_{50}$ of 32 mg/kg p.o. whereas the Example 2a compound exhibits an $ED_{50}$ of about 0.15 mg/kg p.o. Furthermore, the compounds, especially those wherein R is other than hydrogen, lack any significant apomorphine antagonism in rats after administration of from 20 mg/kg s.c. in accordance with the method of Janssen, Arzneimittelforschung 10, 1003–1005 (1960). Additionally, these compounds lack significant cataleptogenic activity in the rat on administration of 20 mg/kg i.p.

For the Example 1 and 2b compounds, the results in the sleep wake cycle and, more relevantly, the H 77/77 test, are similar to those obtained with classical neuroleptics, e.g. loxapine, clothiapine and chlorpromazine. However, the lack of significant activity in the locomotion test, apomorphine test and catalepsy test indicates that the compounds are non-classical neuroleptics, e.g. like clozapine, and do not exhibit significant extrapyramidal effects.

For this use the dosage will, of course, vary depending on the compound employed, mode of administration and treatment desired. However, in general, satisfactory results are obtained when administered at a daily dosage of from about 0.2 mg to about 100 mg per kg animal body weight, conveniently given in divided doses 2 to 4 times a day or in sustained release form. For the larger mammals, the total daily dosage is in the range from about 25 to about 600 mg (e.g. 25 to 100 mg) and dosage forms suitable for oral administration comprise from about 6 mg to about 300 mg (e.g. 6 to 50 mg) of the compounds admixed with a solid or liquid pharmaceutical carrier or diluent.

Additionally, the compounds are useful as sleep-inducing, sleep-promoting and sleep-prolonging agents as indicated in standard tests. For example, the compounds increase the dozing phase and decrease the wake phase in the above-mentioned sleep/wake test.

For this use the dosage will, of course, vary depending on the compound employed, mode of administration and treatment desired. However, in general, satisfactory results are obtained when administered at a daily dosage of from about 0.1 mg to about 20 mg per kg animal body weight, conveniently given in a single dose shortly before retiring to sleep. For the larger mammals, the total daily dosage is in the range from about 10 to about 100 mg, and dosage forms suitable for oral administration comprise from about 2 mg to about 50 mg of the compounds admixed with a solid or liquid pharmaceutical carrier or diluent.

Additionally, the compounds are also useful as antidepressant agents as indicated in standard tests. For example, the compounds inhibit the catalepsy induced by tetrabenazine in rats on i.p. administration of from 1 to 50 mg/kg animal body weight of the compounds in accordance with the method described by Stille, Arzneimittelforschung 14, 534 (1964).

For this use the dosage will, of course vary depending on the compound employed, mode of administration and treatment desired. However, in general, satisfactory results are obtained when administered at a daily dosage of from about 0.05 mg to about 50 mg per kg animal body weight, conveniently given in divided doses 2 to 4 times a day or in sustained release form. For the larger mammals, the total daily dosage is in the range from about 20 to about 100 mg, and dosage forms suitable for oral administration comprise from about 5 mg to about 50 mg of the compounds admixed with a solid or liquid pharmaceutical carrier or diluent.

Furthermore, the compounds exhibit myotonolytic activity, e.g. for relaxing muscles and for the treatment of spastic conditions as indicated in standard tests. For example, in rabbits on i.v. administration of from 0.01 to 5 mg/kg animal body weight a significant muscle relaxing effect is observed in the method of Teschendorf et al, Arch. Exp. Pharmacol. 266, 467-468 (1970).

For this use the dosage will, of course, vary depending on the compound employed, mode of administration and treatment desired. However, in general, satisfactory results are obtained when administered at a daily dosage of from about 0.01 mg to about 5 mg per kg animal body weight, conveniently given in divided doses 2 to 4 times a day or in sustained release form. For the larger mammals, the total daily dosage is in the range from about 1 to about 20 mg, and dosage forms suitable for oral administration comprise from about 0.2 mg to about 10 mg of the compounds admixed with a solid or liquid pharmaceutical carrier or diluent.

The neuroleptic use is the preferred use.

The Example 1 compound exhibits particularly interesting activity, as a neuroleptic.

The compounds are well tolerated, e.g. as regards cardiovascular effects as indicated in by an insignificant blood pressure lowering effect in the infusion cat at from 18.7 to 30 mg/kg i.v.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution of a tablet.

We claim:

1. A pharmaceutical composition useful in treating neuroses, psychoses, depressions or spastic conditions, or for relaxing muscles, or for inducing, promoting or prolonging sleep comprising a pharmaceutically acceptable carrier or diluent and a therapeutically effective amount of a compound of formula I,

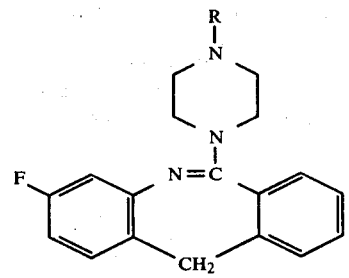

wherein R is hydrogen or $C_{1-4}$ alkyl, or a pharmaceutically acceptable acid addition salt thereof.

2. A method of treating neuroses or psychoses which comprises administering to an animal in need of such treatment a therapeutically effective amount of a compound of formula I,

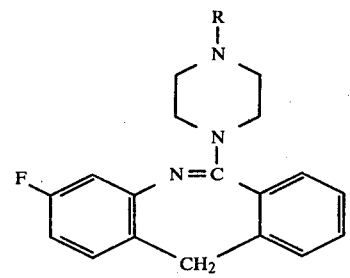

wherein R is hydrogen or $C_{1-4}$ alkyl, or a pharmaceutically acceptable acid addition salt thereof.

3. A method of treating neuroses or psychoses according to claim 2 which comprises administering to an animal in need of such treatment a therapeutically effective amount of a compound of formula I wherein R is methyl, or a pharmaceutically acceptable acid addition salt thereof.

* * * * *